United States Patent
Sanchez Ramos

(10) Patent No.: US 8,075,133 B2
(45) Date of Patent: *Dec. 13, 2011

(54) SAFETY HELMET VISOR WITH A TREATED SURFACE FOR EYE PROTECTION AND THERAPY

(75) Inventor: Celia Sanchez Ramos, Madrid (ES)

(73) Assignee: Universidad Complutense de Madrid, Madrid (ES)

( * ) Notice: Subject to any disclaimer, the term of this patent is extended or adjusted under 35 U.S.C. 154(b) by 490 days.

This patent is subject to a terminal disclaimer.

(21) Appl. No.: 12/175,539

(22) Filed: Jul. 18, 2008

(65) Prior Publication Data

US 2009/0046244 A1 Feb. 19, 2009

Related U.S. Application Data

(60) Provisional application No. 60/972,008, filed on Sep. 13, 2007.

(30) Foreign Application Priority Data

Jul. 19, 2007 (ES) .................................. 200702013

(51) Int. Cl.
*G02C 7/10* (2006.01)
*A42B 3/22* (2006.01)

(52) U.S. Cl. ............................. 351/177; 2/6.3; 351/162
(58) Field of Classification Search .............. 351/160 H, 351/160 R, 162, 163, 177; 2/6.3, 15
See application file for complete search history.

(56) References Cited

U.S. PATENT DOCUMENTS

| 5,528,322 A * | 6/1996 | Jinkerson | 351/163 |
| 2004/0114242 A1 * | 6/2004 | Sharp | 359/498 |

* cited by examiner

*Primary Examiner* — Scott J Sugarman
(74) *Attorney, Agent, or Firm* — Ladas & Parry LLP

(57) ABSTRACT

The invention is a filtering, transparent device for preventing damage to healthy eyes and for the prophylaxis and therapy of pseudophakic eyes and/or eyes with macular and retinal neurodegeneration and is the result of applying a yellow filter to the transparent or translucent surface(s) of the visor of a protective helmet, to protect the eyes from the short wavelengths of the visible spectrum (500 to 380 nm). The invention avoids the difficulties and risks of existing ways of protecting healthy eyes or eyes subjected to cataract surgery, and improve the protection of eyes suffering retinal neurodegeneration, simply by applying a filter to the transparent or translucent surface(s) of the visor of any protective helmet. The invention consists of combining the transparent or translucent surface(s) of the visor of any protective helmet with a yellow filter that absorbs short wavelengths of light from 500 to 380 nm.

12 Claims, No Drawings

SAFETY HELMET VISOR WITH A TREATED SURFACE FOR EYE PROTECTION AND THERAPY

CROSS-REFERENCE TO RELATED APPLICATION

This application is based on and claims priority from Spanish Patent Application No. 200702013, filed on Jul. 19, 2007 and U.S. Provisional Application No. 60/972,008 filed on Sep. 13, 2007, the disclosure of which is incorporated herein in its entirety by reference.

OBJECT OF THE INVENTION

The invention is intended for the ophthalmology sector of the market, within the area of optical applications of a therapeutic and/or prophylactic nature.

The invention is a transparent, filtering device that protects healthy eyes and/or pseudophakic eyes (eyes that have undergone cataract surgery) and/or eyes with macular and retinal degeneration from the short wavelengths of the visible spectrum. It is elaborated by applying a yellow filter to the transparent or translucent surface/s of the visor of a safety helmet to protect the eyes from the short wavelengths of the visible spectrum (500 to 380 nm). As an example, it is indicated for use as a component of protective helmets used by motorcyclists, sports persons, or workers, such as metal welders or other workers exposed to high light intensities.

STATE OF THE TECHNIQUE

Visual perception is the result of the response to visible radiation in the wavelength range 380-760 nm. In the environment, solar radiation is the main risk factor for vision. The sun emits UV rays and IR radiation, which are mainly absorbed by the atmosphere. When the solar radiation transmitted through the atmosphere reaches the Earth's surface it consists of UV-B rays (230-300 nm), UV or UV-A rays (300-380 nm), visible light rays (380-760 nm) and IR rays (760-1400 nm). Healthy human eyes freely transmit IR rays and those of most of the visible spectrum to the retina, but the cornea and crystalline lens prevent the most reactive wavelengths of the visible spectrum (UV-B rays and the blue portion of the spectrum) from reaching the retina.

The human crystalline lens changes its transmission properties as it ages by intensifying its yellowish colour thus increasing its capacity to filter out UV and blue light rays. Hence, in persons older than 65 years, ultraviolet light (<400 nm) is not transmitted and the transmission of blue light (400 -500 nm) is markedly reduced.

The retina is capable of protecting itself from short wavelengths of light in two ways: through its uneven distribution of photoreceptors, such that there are no photoreceptors sensitive to blue light in the macular depression; and through the actions of yellow pigments in this zone, which also exert a protective effect.

These natural protection systems the human eye has against the shorter wavelengths of light—the crystalline lens and structures of the retina—can be seriously affected by certain diseases and/or surgical procedures:

Cataracts, whose surgical treatment involves the removal of the crystalline lens Additionally, it is common to find a pathological ageing process that causes degradation of the retinal structures producing age-related macular degeneration (AMD).

We should also consider that both cataracts and AMD can coexist in persons older than 65 years. In this population of elderly subjects, cataract is the main cause of vision loss and AMD is the main cause of blindness. In addition, we should expect an increase in both these diseases due, among other factors, to our increased life expectancy. This translates into a great interest in these diseases and their treatment options in the research field and optics industry.

Several epidemiological studies have evaluated the relationship between cataract surgery and AMD. Thus, Klein (Klein R, Klein B E, Wong T Y, Tomany S C, Cruickshanks K J. The association of cataract and cataract surgery with the long-term incidence of age-related maculopathy. Arch Ophthalmol 120:1551-1558.2002) and Freeman (Freeman E, Muñoz B, West S K, Tielsch J M, Schein O D. Is there an association between cataract surgery and age-related macular degeneration? Am J Ophthalmol 135(6): 849-856.2003) claim there is a higher risk of developing symptoms of AMD in persons who have undergone cataract surgery. However, in earlier investigations by Wang (Wang J J, Mitchell P, Cumming R G, Lim R. Cataract and age-related maculopathy: the Blue Mountains Eye Study. Ophthalmic Epidemiol 6: 317-326.1999) and McCarty (McCarty C A, Mukesh B N, Fu C L, Mitchell P, Wang J J, Taylor H R. Risks factors for age-related maculopathy: the Visual Impairment Project. Arch Ophthalmol 119:1455-1462.2001) this hypothesis was rejected, possibly because of the less developed technology used for their diagnostic measurements. Techniques such as optical coherence tomography that allow the accurate, rapid and non-invasive follow up of retinal neurodegeneration processes have only recently been introduced. These techniques are essential for establishing the determining effect of the natural pigments that absorb harmful radiations.

Several techniques have also been developed to protect eyes subjected to cataract surgery from short wavelengths of light:

There are several types of filter containing a yellow pigment on the market yet there is no optimal procedure and/or device to apply these filters to the human eye as a preventive and/or therapeutic measure to replace and/or improve the eye's natural protection.

Since the mid-1990s, eyes undergoing cataract extraction have been implanted with intraocular lenses containing a yellow pigment to act as a filter. This option requires surgical intervention with all its risks and difficulties. There is also a large population of subjects who have been implanted with a transparent lens to replace the natural lens during cataract surgery who are therefore devoid of the necessary protection. In these patients, the artificial lens, lacking a yellow pigment, needs to be complemented with a system to support the yellow pigment, for example, the safety helmet visor proposed here.

Several patents related to the state of this technique have been developed although they differ considerably from the object of the present invention:

Protective helmet with sunshade (patent EP1498041)

Glasses for helmets and helmets fitted with these glasses (patent EP1601260)

Day and night vision device (patent EP1681853) for use in telescopes and military helmets Method of increasing the brightness of daylight using a device mounted on a helmet (patent EP1564578)

These devices differ from the present invention mainly in their purpose and utility since none has been designed as a preventive measure to protect eyes from short wavelengths of light.

Moreover, most of these patents do not refer to the application of a filter to the transparent surface/s of the visor of a protective helmet rather they describe other formats (light devices, lenses, solutions etc.).

DESCRIPTION OF THE INVENTION

The general objective of this invention is to prevent damage to the eyes by protecting them from absorbing blue and violet light through the application of a filter to the transparent or translucent surface(s) of a protective helmet visor. As mentioned earlier, it is particularly useful in the case of pseudophakic persons, to functionally compensate for their lack of protective pigments (removed during surgery), and as prophylaxis for subjects suffering retinal neurodegeneration. Both these conditions are common among elderly persons but the invention is equally important for protecting healthy eyes in any subject.

The invention is prepared by applying to the transparent or translucent surface(s) of a protective helmet visor, a yellow filter that absorbs short wavelengths of light from 500 to 380 nm. As an example, several possible applications are indicated such as its use in helmets used by motorcyclists, sports persons, metal or other workers, etc.

The invention combines three components:
  A visor for a protective helmet that has a transparent or translucent surface(s)
  A frame or system to apply the filter to the transparent or translucent surface(s) of the visor
  A filter containing one of the yellow pigment dyes available on the market, which is suitable for application to the visor surface material, that absorbs short wavelengths of light from 500 to 380 nm across the surface's entire area of light transmission The following procedure can be used to prepare the invention:
  A yellow filter is prepared using those available on the market, for example, in the form of a screen or dye. The filter should be compatible with the surface to which it will be applied.
  A supporting material or device is prepared from those available on the market to apply the filter to the transparent or translucent surface(s) of the visor, according to the manufacturer's instructions
  The yellow filter is applied to or mounted on the visor surface(s), such that the whole light transmitting area is covered
  The visor is then fitted to the protective helmet according to the manufacturer's instructions In conclusion, the combined use of the transparent or translucent surface(s) of a protective helmet visor and a yellow filter will protect from the harmful effects of short wavelengths of light: the healthy eyes of any subject, the eyes of patients operated on for cataract implanted with a transparent intraocular lens (by supplementing their unprotected artificial lens) and the eyes of persons suffering retinal neurodegeneration (by improving their natural protection). This system avoids the problems related to the options available on the market (e.g., filters with no support system, intraocular lenses).

HOW TO PREPARE THE INVENTION

There are several ways of preparing the invention, depending on the material of the surface to which the filter will be applied. The following example illustrates how the invention can be elaborated but is in no way restrictive and there are many other ways or combinations that can be used.

EXAMPLE 10.3 mg of a conventional yellow dye such as 4-phenylazophenol, or Solvent Yellow 7 (SY7), are dissolved in 10.01 g of a monomer solution containing 66% PEA, 30.5% PEMA and 3.3% BDDA, to give a final SY7 concentration of 0.103 wt %.

52.3 mg of bi 4-tert-butylcyclohexylperoxide bicarbonate are then added as a polimerization catalyst.

Using a syringe, the solution is introduced in a mould formed by two overlapping glass plates joined by metal clips and a 1 mm Teflon ring. The solution is extended as 2.5 mm sheets.

Polymerization takes place when the mould is introduced in an oven at 65° C. for 17 hours. The temperature of the oven is later increased to up to 100° C. for a further 3 hours.

Once polymerization is complete, the sheet is extracted from the mould, and after the appropriate measurements have been made, the filter is cut to the desired size.

The invention claimed is:

1. A method for protecting a subject having a pseudoaphakic eye implanted with a transparent intraocular lens in an activity during which the eye is exposed to short wavelengths of light, the method comprising the steps of:
   (a) providing a helmet with a protective visor comprising a yellow dye that absorbs wavelengths of light from 500 to 380 nm; and
   (b) putting the helmet on the head of the subject so that the visor protects the eye from the short wavelengths of light during the activity.

2. The method as claimed in claim 1, wherein the activity is selected from the group consisting of motorcycle riding, a sport and welding.

3. The method as claimed in claim 1, wherein the activity is a water sport or skiing.

4. The method as claimed in claim 1, wherein the activity is one in which the subject is exposed to intense light.

5. The method as claimed in claim 1, wherein the protective visor is provided by applying a filter comprising the yellow dye to a surface of a transparent or translucent visor and the protective visor is then fitted to the helmet.

6. The method as claimed in claim 5, wherein the yellow dye comprises 4-phenylazophenol.

7. A method for protecting a subject having an eye with retinal neurodegeneration in an activity during which the eye is exposed to short wavelengths of light, the method comprising the steps of:
   (a) providing a helmet with a protective visor comprising a yellow dye that absorbs wavelengths of light from 500 to 380 nm; and
   (b) putting the helmet on the head of the subject so that the visor protects the eye from the short wavelengths of light during the activity.

8. The method as claimed in claim 7, wherein the activity is selected from the group consisting of motorcycle riding, a sport and welding.

9. The method as claimed in claim 7, wherein the activity is a water sport or skiing.

10. The method as claimed in claim 7, wherein the activity is one in which the subject is exposed to intense light.

11. The method as claimed in claim 7, wherein the protective visor is provided by applying a filter comprising the yellow dye to a surface of a transparent or translucent visor and the protective visor is then fitted to the helmet.

12. The method as claimed in claim 11, wherein the yellow dye comprises 4-phenylazophenol.

* * * * *